Figure 1:
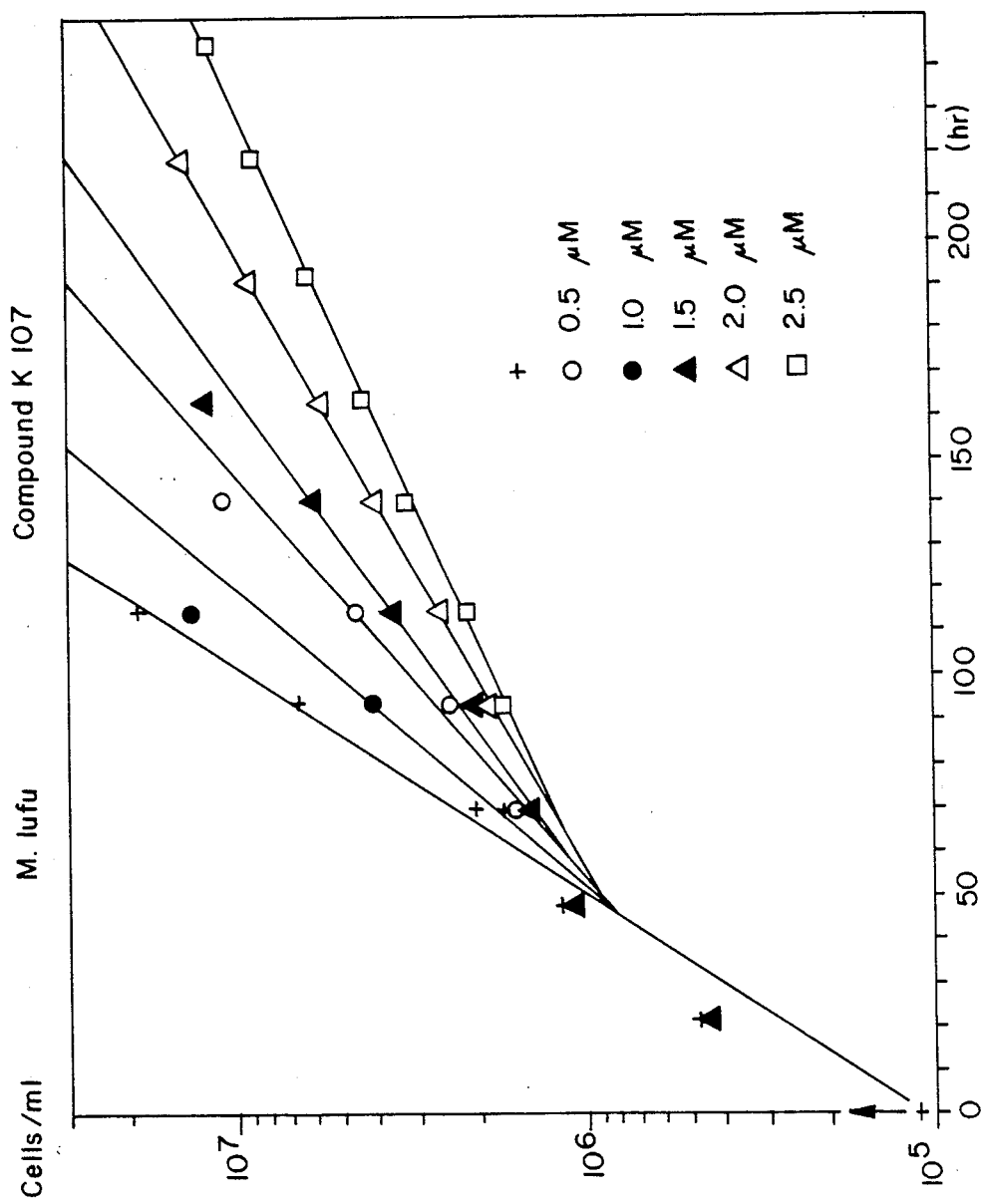

United States Patent [19]

Seydel et al.

[11] Patent Number: 4,912,112

[45] Date of Patent: Mar. 27, 1990

[54] SUBSTITUTED 2,4-DIAMINO-5-BENZYLPYRIMIDINES, THEIR PREPARATION AND THEIR USE AS MEDICAMENTS WITH AN ANTIMICROBIAL ACTIVITY

[75] Inventors: Joachim Seydel, Borstel; Rolf Haller; Manfred Kansy, both of Kiel; Gerd Hachtel, Raisdorf, all of Fed. Rep. of Germany

[73] Assignee: Saarstickstoff-Fatol GmbH Chem.-Pharm. Fabrik, Schiffweiler, Fed. Rep. of Germany

[21] Appl. No.: 11,957

[22] Filed: Feb. 6, 1987

[30] Foreign Application Priority Data

Feb. 6, 1986 [DE] Fed. Rep. of Germany ....... 3603577

[51] Int. Cl.$^4$ ................. C07D 239/49; A61K 31/505
[52] U.S. Cl. ..................................... 514/275; 544/325

[58] Field of Search .......................... 544/325; 514/275

[56] References Cited

U.S. PATENT DOCUMENTS

| | | |
|---|---|---|
| 4,115,650 | 9/1978 | Manchand ............................ 544/325 |
| 4,143,227 | 3/1979 | Rosen ................................... 544/325 |
| 4,515,948 | 5/1985 | Kompis et al. ....................... 544/325 |

*Primary Examiner*—John M. Ford
*Attorney, Agent, or Firm*—Cushman, Darby & Cushman

[57] ABSTRACT

Novel substituted 2,4-diamino-5-benzyl pyrimidines are described. The novel substances have antimicrobial activity and are particularly suitable for inhibiting the growth of mycobacteria. Combined with inhibitors such as diaminodiphenylsulphones, ring-substituted 4-aminodiphenylsulphones or ring and/or nitrogen-substituted diaminodiphenylsulphones, they have a marked synergistic activity.

21 Claims, 2 Drawing Sheets

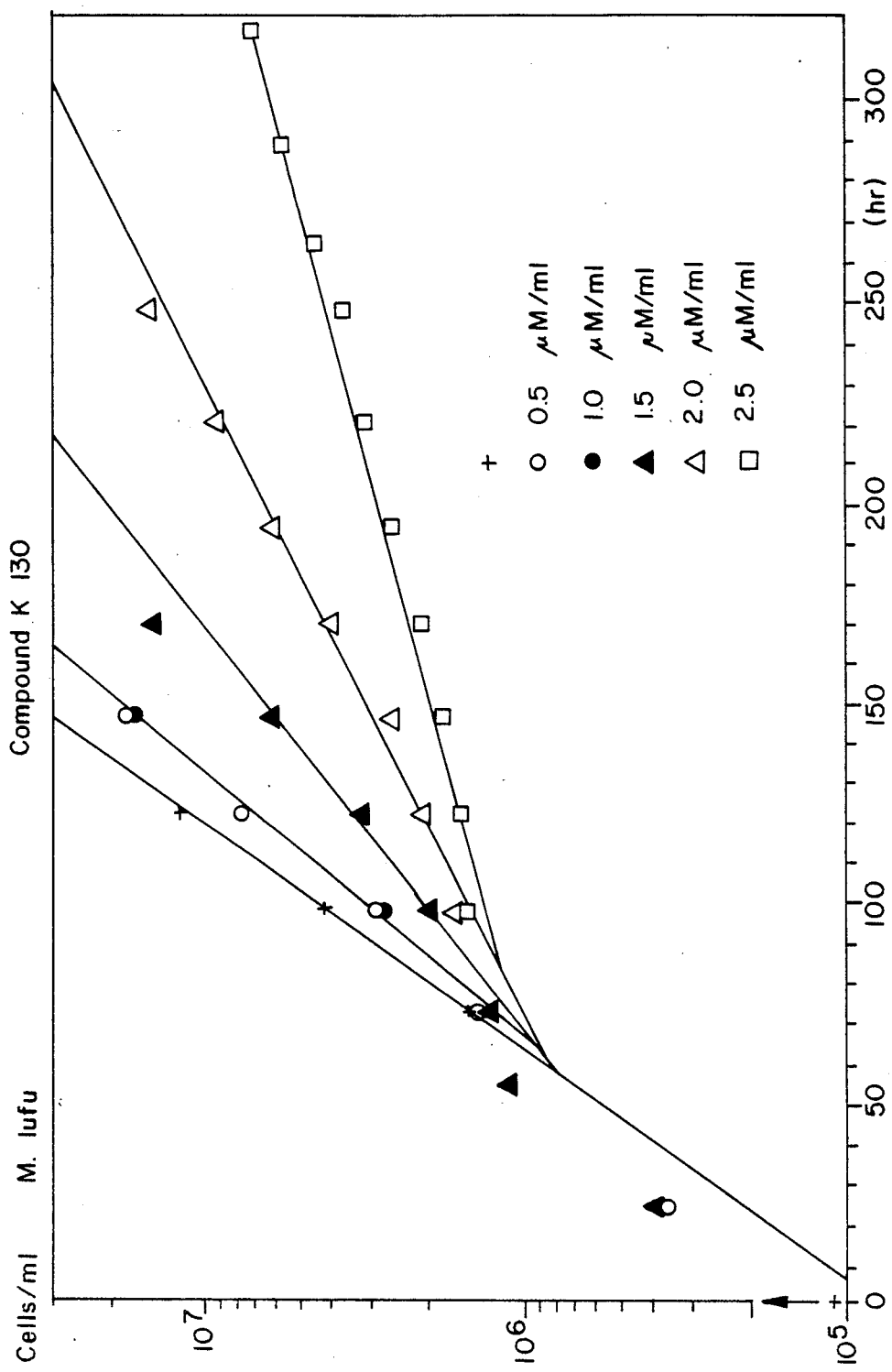

SUBSTITUTED 2,4-DIAMINO-5-BENZYLPYRIMIDINES, THEIR PREPARATION AND THEIR USE AS MEDICAMENTS WITH AN ANTIMICROBIAL ACTIVITY

The invention relates to novel substituted 2,4-diamino-5-benzylpyrimidines, their preparation and their use as medicaments for the treatment of microbial and in particular mycobacterial infections.

The antibacterial activity of compounds of the benzylpyrimidinetype is known. Such compounds, such as e.g. the known products trimethoprim, brodimoprim and tetroxoprim exert their activity by inhibiting dihydrofolic acid reductase (DHFR) in the case or Gram negative and Gram positive bacteria. However, it has been found that these compounds have only an extremely limited activity with respect to mycobacteria. With these agents the concentrations necessary for inhibiting mycobacterial growth are so high, that they cannot be attained in vivo or are not acceptable.

The problem of the present invention is therefore to provide compounds, which in low physiologically acceptable concentrations constitute effective inhibitors of microbial growth and particularly mycobacterial growth.

According to the invention this problem is solved by the novel substituted 2,4-diamino-5-benzylpyrimidines of general formula I

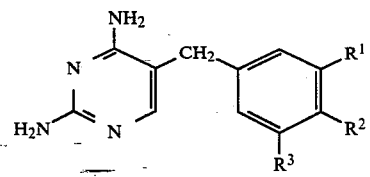

in which one of the substituents $R^1$ to $R^3$ (i) is an alkoxy or alkylthio group with more than 4 carbon atoms and advantageously 4 to 10 carbon atoms, a phenylalkoxy, phenylalkylthio, phenoxyalkoxy, phenoxyalkylthio, phenylaminoalkoxy, phenylaminoalkylthio group with 3 to 6 C atoms in the alkyl chain or a, cycloalkoxy, cycloalkylthio, cycloalkylalkylthio or cycloalkylalkoxy group wherein the cyclic radical as well as the alkyl chain have 3 to 6 carbon atoms respectively or (ii) a 2',4'-substituted phenyl-4-sulphonylphenyl aminoalkoxy, phenyl-4-sulphonylphenyl-aminoalkylthio, phenyl-4-sulphonylphenylalkoxy or phenyl-4-sulphonylphenylakylthio group, in which the substituents in the 2',4'-position are the same or different and are hydrogen, amino, alkylamino, dialkylamino, alkoxy, alkyl, nitro, alkylthio and/or acetamino groups wherein the alkyl radical has 1 to 6 C-atoms in the chain and the two others of the substituents $R^1$ to $R^3$ are the same or different and are hydrogen, alkoxy, alkylthio and/or alkylamino groups.

The alkyl radical of the two other substituents $R^1$ to $R^3$ preferably has 1 to 3 C-atoms and in particular 1 C-atom.

Representative examples of compounds of the invention include 2,4-diamino-5-(4-propoxyphenyl-benzyl)-pyrimidine; 2,4-diamino-5-(4-propoxyphenyl-3-methoxy-benzyl)-pyrimidine; 2,4-diamino-5-(4-pentloxy-3-methoxybenzyl)-pyrimidine; 2,4-diamino-5-(4-hexyloxy-3-methoxybenzyl)-pyrimidine; 2,4-diamino-5-(4-heptyloxy-3-methoxybenzyl)-pyrimidine; 2,4-diamino-5-(4-octyloxy-3,5-dimethoxybenzyl)-pyrimidine; 2,4-diamino-5-(4-nonyloxy-3,5-dimethoxybenzyl)-pyrimidine; 2,4-diamino-5-(4-decyloxy-3-methoxybenzyl)-pyrimidine; 2,4-diamino-5-[3,5-dimethoxy-4-(4'-nitrophenyl-4-sulphonylphenyl)-methoxybenzyl]-pyrimidine; 2,4-diamino-5-(3,5-dimethoxy-4-[3-(4'-nitrophenyl-4-sulphonylphenylamino)propoxy]benzyl)-pyrimidine; 2,4-diamino-5-(4-methoxy-3-[2-(4'-nitrophenyl-4-sulphonylphenylamino)ethoxy]benzyl)-pyrimidine; 2,4-diamino-5-(4-methoxy-3-[3-(4'-nitrophenyl-4sulphonylphenylamino)propoxy]benzyl)-pyrimidine; 2,4-diamino-5[4-(4'-aminophenyl-4-sulphonylphenylmethoxy)-3,5-dimethoxybenzyl]-pyrimidine; 2,4-diamino-5-(4-[3-(4'-aminophenyl-4-sulphonylphenylamino)-propoxy]-3,5-dimethoxybenzyl)-pyrimidine; 2,4-diamino-5-[3-(4'-aminophenyl-4-sulphonylphenylmethoxy)-4-methoxybenzyl]-pyrimidine; 2,4-diamino-5-(3-[2-(4'-aminophenyl-4-sulphonylphenylamino)-ethoxy]-4-methoxybenzyl)-pyrimidine; 2,4-diamino-5-(4-[3-(4-aminophenyl-4-sulphonylphenylamino)propoxy]-3,5-dimethoxybenzyl)-pyrimidine; 2,4-diamino-5-(4'-aminophenyl-4-sulphonylphenylmethoxy)-3-methoxybenzyl]pyrimidine; 2,4-diamino-5-(4-[3-(4'-methylphenyl-4-sulphonylphenylamino) -propoxy]-3,5-dimethoxybenzyl)-pyrimidine; 2,4-diamino-5-(4-[2-(4'-aminophenyl-4-sulphonylphenylamino)ethoxy]-3,5-dimethoxybenzyl)-pyrimidine; 2,4-diamino-5-(4-[2-(2'-methyl-4'-aminophenyl-4-sulphonylphenylamino)ethoxy)-3,5-dimethoxybenzyl)-pyrimidine.

According to the invention, it has surprisingly been found that the introduction of substituents according to formula I into compound of the benzylpyrimidine type leads to a dramatic increase in the activity of these compounds as mycobacterial growth inhibitors (cf. table 1).

The inventive substituted 2,4-diamino-5-benzylpyrimidines can be prepared in that for obtaining compounds according to formula I (i)

(aa) a compound of general formula II

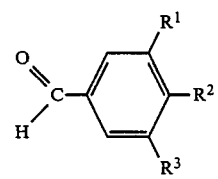

in which one or the substituents $R^1$ to $R^3$ is a hydroxyl or a mercapto group and the two other of the substituents $R^1$ to $R^3$ are the same or different and are hydrogen, alkoxy, alkylthio and/or alkylamino groups is etherified with a halide suitable for forming an alkoxy, alkylthio, phenylalkoxy, phenylalkylthio, phenylalkoxy, phenoxyalkylthio, phenylaminoalkoxy, phenylaminoalkylthio, cycloalkoxy, cycloalkylthio, cycloalkylalkylthio or cycloalkylalkoxy group, (ab) the compound obtained in stage aa) is condensed with a β-morpholinopropionitrile, (ac) the compound obtained in stage ab) is reacted with aniline and (ad) the compound obtained in stage ac) is cyclized with guanidine.

For the preparation of compounds according to formula I (ii) it is possible to either (ba) a compound of general formula III

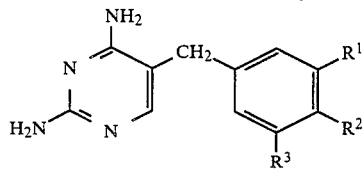

in which one of the substituents $R^1$ to $R^3$ is a hydroxyl or a mercapto group and the two other of the substituents $R^1$ to $R^3$ are the same or different and are hydrogen, alkoxy, alkylthio and/or alkylamino groups is etherified with a compound of general formula IV

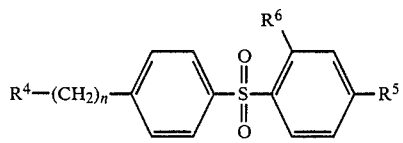

or formula V

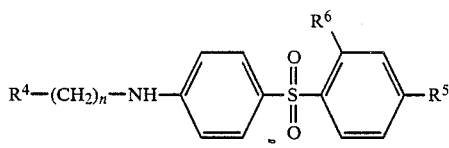

in which $R^4$ is a halogen radical and $R^5$ and $R^6$ are the same or different and are hydrogen, amino, alkylamino, dialkylamino, alkoxy, alkyl, nitro, alkylthio and/or acetamino groups.

Etherification appropriately takes place in per se known manner in solvents such a water, methanol, ethanol, n-propanol, isoproaanol, butanol, dimethylformamide, dimethylsulphoxide, acetone, methylethylketone and monoalkylated and dialkylated ethers of ethyleneglycol and diethyleneglycol and mixtures thereof, accompanied by the addition or a base such as sodium, sodium ethoxide, sodium or potassium hydroxide, potassium or sodium carbonate at a temperature between −20° C. and the boiling point of the solvent used, but preferably at ambient temperature.

According to a preferred embodiment of the invention, etherification is carried out in ethyleneglycol monomethylether as the solvent and the sodium alkoxide of the ethyleneglycol monomethylether.

The compounds according to formula I (ii) can also be prepared in that
(bb) a compound of general formula VI

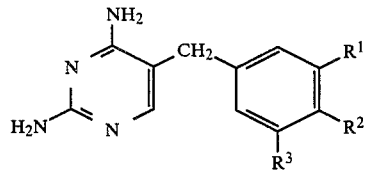

is reduced, in which one of the substituents $R^1$ to $R^3$ is a 2′,4′ substituted phenyl-4-sulphonylphenylaminoalkoxy, phenyl-4-sulphonylphenylaminoalkylthio, phenyl-4-sulphonylphenylalkoxy or phenyl-4-sulphonylalkylthio group with a terminal nitro group, the substituents in the 2 ′4′-position being the same or different and hydrogen, amino, alkylamino, dialkylamino, alkoxy, alkyl, nitro, alkylthio and/or acetamino groups and the two other of the substituents $R^1$ to $R^3$ are the same or different and are hydrogen, alkoxy, alkylthio and/or alkylamino groups.

Reduction is appropriately carried out in per se known manner in solvents such as water, methanol, ethanol, glacialacetic acid, ethylacetate, dimethylformamide, water/ethanol, water/dioxan, water tetrahydrofuran, ethyleneglycol monomethylester and further alkyl and aryl ethers of ethylene glycol, diethyleneglycol and mixtures thereof in the presence of a hydrogenating catalyst such as Raney nickel, platinum or palladium/charcoal. Reduction can take place with metals such as iron, tin or zinc in the presence of an acid such as hydrochloric or acetic acid, with salts such as ferrous sulphate, stannous chloride/hydrochloric acid or sodium dithionide in the presence of a base such as sodium hydroxide solution, pyridine or hydrazine and Raney nickel, the temperatures being between 0° and 100° C., but preferably 50° C.

It has proved to be particularly advantageous to carry out the reduction in ethyleneglycol monomethylether, methanol or mixtures thereof at 50° C, 1 to 6 bar and in the presence of Raney nickel W2 (produced in accordance with Org. Synth. Coll. 3, 181, 1955) or palladium/charcoal.

The effectiveness of the compounds according to the invention as growth inhibitors for in particular mycobacteria was proved on bacterial cell cultures by determining the minimum inhibiting concentrations and the concentrations necessary for half maximum growth inhibition ($I_{50}$) when using typical representatives of the inventive compounds.

There was surprisingly found to be an up to 300 times increased activity of the inventive compounds compared with commercially available products, such as e.g. pyrimethamine. There was also found to be a synergistic effect of combinations of the claimed compounds and inhibitors of dihydropteroic acid synthetase, such as e.g. with diaminodiphenylsulphone (DDS).

The inventive compounds can therefore be used as active ingredients in medicaments for the treatment of microbial infections and in particular mycobacterioses either alone or combined with inhibitors such as diaminodiphenylsulphones, ring-substituted 4-aminodiphenylsulphones or ring and/or nitrogen-substituted diaminodiphenylsulphones and/or antibacterially acting sulphonamides. Their importance lies inter alia in the possibility of treating both partially DDS and TMP-resistant mycobacterioses and avoiding the development of resistance in the case of DDS or TMP monotherapy.

The inventive medicaments contain the active substances of the invention or active substance combinations together with a pharmaceutically acceptable carrier. The latter can be an organic or inorganic carrier material suitable for enteral, percutaneous or parenteral administration, such as e.g. water, gum Arabic, lactose, starch, magnesium stearate, tallow, vegetable oils, polyalkyleneglycols, vaseline and the like. The products can also contain other pharmaceutically active substances, such as antipyrific agents, pain relieving agents, anti-inflammatory agents and the like. The pharmaceutical products can be administered orally, e.g. in the form of tablets, capsules, pills, powders, granules, solutions, syrups, suspensions, elixirs and the like. However, administration can also by effected parenterally, e.g. in the form or sterile solutions, suspensions or emulsions or locally in the form of suspensions, ointments, powders, aerosols and the like.

The pharmaceutical products can also be sterilized and/or contained constituents such as preservatives, stabilizers, wetting agents, emulsifiers, salts and buffer substances.

The invention is illustrated hereinafter by means of examples.

EXAMPLE 1

Preparation of 2,4-diamino-5-(4-decyloxy-3-methoxybenzyl)-pyrimidine (GH 310)
(a) 4-decyloxy-3-methoxybenzaldehyde:

30.4 g (0.2 mole) of vanillin and 48.7 g (0.22 mole) of 1 bromodecane ar dissolved, accompanied by stirring, in a solution of 5.75 g (0.25 mole) of sodium in 300 ml of ethyleneglycol monomethylether. The solution was heated to boiling or 18 hours, mixed with 200 ml of water and cooled. The crystallized substance was removed by suction and recrystallized from methanol. White crystals with a melting point of 51° C. were obtained.

(b) 3-morpholino-2-(4-decyloxy-3-methoxybenzyl)-acrylonitrile (E/Z mixture):

29.2 g (0.1 mole) of 4-decyloxy-3-methoxybenzaldehyde and 14.5 g (0.11 mole) of β-morpholinopropionitrile were heated to 65° C. in 150 ml of dimethylsulphoxide. Accompanied by vigorous stirring, 1.6 g (0.02 mole) of sodium methoxide were introduced, the temperature rising to approximately 75° C. After 30 minutes, 200 ml of water were added and the product extracted with dichloromethane. A yellow-brown oil was obtained as the crude product.

(c) 3-anilino-2-(4-decyloxy-3-methoxybenzyl)-acrylonitrile (E/Z mixture):

20.7 g (0.05 mole) of 1-morpholino-2-(4-decyloxy-3-methoxybenzyl)-acrylonitrile, 4.7 g (0.05 mole) of aniline and 4.1 ml of concentrated hydrochloric acid were heated to boiling for 1 hour in 70 ml of 2-propanol. After cooling to 4° C, the precipitated substance was removed by suction and recrystallized from methanol. White crystals with a melting point of 80° to 99° C. were obtained.

(d) 2,4-diamino-5-(4-decyloxy-3-methoxybenzyl)-pyrimidine:

16.8 g (0.04 mole) of 1-aniline-2-(4-decyloxy-3methoxybenzyl)acrylonitrile, 5.7 g (0.06 mole) of guanidine hydrochloride and 4.9 g (0.09 mole) of sodium methoxide were heated to boiling for 24 hours, accompanied by vigorous stirring, in 60 ml of absolute ethanol. Following cooling, the resulting substance was removed by suction, washed with water and methanol and recrystallized from methanol. White crystals with a melting point of 138° C. were obtained.

The following compounds were prepared in the same way as in the processes according to (a) to (d):

2,4-diamino-5-(4-propoxyphenyl-benzyl)-pyrimidine, GH 003, melting point 169° C.

2,4-diamino-5-(4-propoxyphenyl-3-methoxy-benzyl)-pyrimidine, GH 103, melting point 139° C.

2,4-diamino-5-(4-pentyloxy-3-methoxybenzyl)-pyrimidine, GH 305, melting point 157° C.

2,4-diamino-5-(4-hexyloxy-3-methoxybenzyl)-pyrimidine, GH 306, melting point 147° C.

2,4-diamino-5-(4-heptyloxy-3-methoxybenzyl)-pyrimidine, GH 307, melting point 145° C.

2,4-diamino-5-(4-octyloxy-3,5-dimethoxybenzyl)-pyrimidiee, GH 308, melting point 152° C.

2,4-diamino-5-(4-nonyloxy-3,5-dimethoxybenzyl)-pyrimidine, GH 309, melting point 128° C.

EXAMPLE 2

Preparation of 2,4-diamino-5-[3,5-dimethoxy-4-(4'-nitrophenyl-4-sulphonylphenyl)-methoxybenzyl]-pyrimidine (K 95) 2.76.g (0.01 mole) of 2,4-diamino-5-(4-hydroxy-3,5-dimethoxybenzyl)-pyrimidine (J. Med. Chem., 14, 58, 1971) were dissolved by stirring in a solution of 0.23 g (0.01 mole) of sodium in 45 ml or ethyleneglycol monomethylether. This was followed by the addition of 3.92 g (0.011 mole) of 4-bromomethyl-4'-nitrodiphenylsulphone (J. Chem. Soc., 22, 1508, 1957) and stirring took place for 17 hours at ambient temperature.

The end product was precipitated by introducing HCl gas, followed by suction filtering and dissolving in a mixture of 30 ml of ethylene glycol monomethylether and 10 ml of acetone, accompanied by heating and the addition or concentrated ammonia and a little water. Until the first permanent turbidity occurred, mixing slowly took place with water in the boiling heat, following by cooling to room temperature and the filtering off of the precipitated crystals. The crude product was recrystallized from ethyleneglycol monomethylether/water (see above). Yellow crystals with a melting point of 225 ° to 229° C. were obtained (accompanied by decomposition).

EXAMPLE 3

Preparation of 2,4-diamino-5-(3,5-dimethoxy-4-[2-(4'-nitrophenyl-4-sulphonylphenylamino)ethoxy]-benzyl)-pyrimidine (K (a) 4-[N-(2-bromomethyl)-N-tosylamino]-4'-nitrodiphenylsulphide (Anand et al, J. Sci. Industr. Res., 13B, pp.260-269, 1954).

40.05 g (0.1 mole) of 4-tosylamino-4'-nitrodiphenylsulphide (Baker et al, J. Org. Chem., 15, 400, 1950) and 376 g (2.0 mole) of 1,2-dibromomethane were heated to boiling for a total of 24 hours in 540 ml of ethanol and following the addition of 100 mg of Cu(I)J and a solution of 8 g of potassium hydroxide in water. After 12 hours, again 8 g of potassium hydroxide in 20 ml of water were added and further heating to boiling took place. The mixture was rotated to approximately 150 ml, the precipitated substance was filtered off, washed with water and dried. For purification purposes, the product was dissolved in methylene chloride and purified with activated carbon or recrystallized from ethylacetate. In both cases, white-yellowish crystals were obtained with a melting point of 133 to 135° C.

(b) 4-[N-(2-bromomethyl)-N-tosylamino]-4'-nitrodiphenylsulphone (Anand et al see above).

40.5 g (0.08 mole) of 4-N-(2-bromomethyl)-N-tosylamino-4'-nitrodiphenylsulphide were stored for 4 hours on the water bath at 65° .C in a mixture of 94 ml of concentrated hydrogen peroxide solution and 500 ml of glacial acetic acid. By diluting with 1000 ml of water and cooling in the icebath, the end product was completely precipitated, filtered off, washed with water and well dried. White crystals with a melting point of 182° to 184° C. were obtained.

(c) 4-[N-(2-bromomethyl)-amino]-4'-nitrodiphenylsulphone (Anand et al, see above)

16.2 g (0.03 mole) of dried 4-[N-(2-bromomethyl)-N-tosylamino]-4'-nitrodiphenylsulphone were mixed with 32.5 ml of concentrated sulphuric acid and stirred for precisely 1 hour at room temperature. Then, accompanied by stirring, the mixture was poured onto 300 ml of ice and 200 ml of water were added. The precipitated yellow product was filtered off and washed with water. The substance was then dissolved in 250 ml of acetone, accompanied by stirring and then adjusted to pH 9 with dilute ammonia. The solution was rotated in vacuo to 100 ml, again poured on to 500 ml of ice and the precipitated substance was filtered off. Recrystallization then took place from ethylacetate or acetone/water. Yellow crystals with a melting point or 164° to 167° C. were obtained.

(d) 2,4-diamino-5-(3,5-dimethoxy-4-[2-(4'-nitrophenyl-4-sulphonylphenyl-amino)-ethoxy]-benzyl)-pyrimidine.

An alkoxide solution was prepared from 0.3 g (0.013 mole) of sodium and 200 ml of ethyleneglycol monomethylether. 3.5 g (0.0126 mole) of 2,4-diamino-5-(4-hydroxy-3,5-dimethoxybenzyl)-pyrimidine according to example 2 were added and the solution stirred until the phenol has completely dissolved giving a red colour. 0.1 g of NaJ and 4.9 g (0.0127 mole) of 4-[N-(bromoethylamino)]-4'-nitrodiphenylsulphone were added and the solution was stirred for 4 days at room temperature. The mixture was poured on to 400 ml of ice, the precipitated substance was filtered off, dried and dissolved whilst heating in 250 ml of acetone. The solution was filtered, rotated to approximately 5 ml in vacuo and purified over a column, diameter 6.5 cm, length 30 cm, silica gel (particle size corresponding to an internal mesh size of 0.21 to 0.063 mm, 300 g) with a mobile solvent mixture of 80 parts methylene chloride, 20 parts n-propanol and 1 part of concentrated ammonia. The pure substance fractions were combined and rotated to 20 ml giving a yellow substance, which was filtered off after cooling overnight. Yellow crystals with a melting point or 235° to 238° C. were obtained (accompanied by decomposition).

EXAMPLE 4

Preparation of
2,4-diamino-5-(3,5-dimethoxy-4-[3-(4'-nitrophenyl-4-sulphonylphenylamino)-propoxy]-benzyl)-pyrimidine
(K 122)

(a) 4-[N[(3-bromopropyl)-H-tosylamino]-4'-nitrodiphenylsulphide:

40.05 g (0.1 mole) of 4-tosylamino-4'-nitrodiphenylsulphide according to example 3 (a) and 150 ml (1.5 mole) of 1,3-dibromopropane in 500 ml of ethanol were heated to boiling after adding 01 g of Cu(I)J. A solution or 14 g of potassium hydroxide in 30 ml of water was slowly added dropwise to the boiling solution within 8 hours and boiling took place for a further 2 hours. The ethanol was removed under reduced pressure and excess dibromopropane by means of steam distillation. The remaining residue was cooled, dissolved accompanied by heating in 300 ml of ethylacetate, mixed with 4 g of activated carbon and filtered. The solution was mixed with 200 ml of ethanol, rotated to approximately half, placed cool, the precipitated crystals were filtered off and then recrystallized in ethylacetate. Crystals of melting point 112° to 114° C. were obtained.

(b) 4-[N-(3-bromopropyl)-N-tosylamino]-4'-nitrodiphenylsulphone:

36.5 g (0.07 mole) of 4-[N-(3-bromopropyl)-N-tosylamino]-4'-nitrodiphenylsulphide were stirred for 4 hours at 65° C. accompanied by the addition of 80 ml of concentrated hydrogen peroxide solution in 400 ml of glacial acetic acid. The solution was diluted with 900 ml of water as in example 3 b) and the end product completely precipitated by cooling in the icebath. Recrystallization took place in methanol, accompanied by the addition of a little methylene chloride. White crystals of melting point 153 to 155° C. were obtained.

(c) 4-[N-(3-bromopropyl)-amino]-4'-nitrodiphenylsulphone:

10 g (0.018 mole) of 4-[N-bromopropyl)-N-tosylamino]-4'-nitrodiphenylsulphone were mixed with 20 ml of concentrated sulphuric acid and stirred for precisely 60 minutes at ambient temperature. Accompanied by stirring, the mixture was then poured on to 500 ml of ice, filtered off, washed with water and dissolved in 150 to 200 ml of acetone, accompanied by heating. The solution was then adjusted with concentrated ammonia to pH 9, filtered, completely concentrated by evaporation in vacuo and cooled. Recrystallization then took place in methanol, accompanied by the addition of a little methylene chloride. Yellow crystals of melting point 130° to 132° C. were obtained.

(d) 2,4-diamino-5-(3,5-dimethoxy-4-[3-(4'-nitrophenyl-4-suphonylphenylamino)-propoxy]-benzyl)-pyrimidine:

0.35 g (0.015 mole) of sodium were dissolved in 100 ml of ethyleneglycol monomethylether, 4.2 g (0.015 mole) of 2,4-diamino-5-(4-hydroxy-3,5-dimethoxybenzyl)-pyrimidine (cf. example 2) were added and stirred until the phenol had completely dissolved. The solution was then mixed with 0.1 g of NaJ and 6.2 g (0.155 mole) of 4-[N-(3-bromopropyl)-amino]-4'-nitrodiphenylsulphone and stirred for 3 days at ambient temperature.

The mixture was mixed with 500 ml of ice, filtered, washed with water, dissolved in 300 to 400 ml of acetone accompanied by heating, filtered again and rotated in vacuo to 75 to 100 ml. This solution was kept overnight at 5° C. and the precipitated crystals filtered off. This was followed by recrystallization in methanol, accompanied by the addition of a little methylene chloride. Yellow crystals with a melting point of 210° to 213° C. were obtained.

EXAMPLE 5

Preparation of
2,-diamino-5-[4-methoxy-3-(4'-nitrophenyl-4-sulphonylphenyl)-methoxybenzyl]-pyrimidine (K 127)

(a) 3-benzyloxy-4-methoxybenzaldehyde:

A phenolate solution was prepared from 21.6 g (0.4 mole) of sodiummethoxide and 60.9 g (0.4 mole) of 3-hydroxy-4-methoxybenzaldehyde in 350 ml of ethyleneglycol monometylether. The solution was heated to 100° C, 51 g (0.4 mole) of benzylchloride were added and stirring took place for 2 hours at this temperature. The mixture was cooled to ambient temperature, mixed with 600 ml of water and placed cool. The crude product was filtered off, recrystallized from methanol, dried and further processed. White crystals of melting point 62° to 63° C. were obtained.

(b) 3-benzyloxy-4-methoxy-morpholinomethylidenedihydrocinnamicnitrile:

Accompanied by heating to 65° C, 89.6 (0.37 mole) of 3-benzyloxy-4-methoxybenzaldehyde were dissolved in 500 ml of dimethylsulphoxide. Successively 57 g (0.4 mole) of 3-morpholinopropionitrile and 4.5 g (0.083 mole) of sodiummethoxide were added, the temperature rising to over 70° C. Stirring took place for a further 15 minutes at 65° C., followed by cooling to room temperature, mixing the solution with a mixture of 750 ml of isoproponol/water (1:10) and cooling overnight a 5° C. The crude product was extracted with methylene chloride, the combined methylene chloride phases were well dried over sodium sulphate and evaporated to dryness in vacuo. The viscous crude product was directly further processed.

(c) Anilinomethyliene-3-benzyloxy-4-methoxy-dihydrocinnamicnitrile:

72.9 (0.2 mole) of 3-benzyloxy-4-methoxymorpholinomethylidene-dihydrocinnamicnitrile in 250 ml of isopropanol were mixed with 22.3 g (0.24 mole) of aniline and 27 ml of concentrated hydrochloric acid and heated to boiling for 1 hour. The mixture was allowed to cool to room temperature, the precipitated substance was filtered off and washed with water and diethylether. Recrystallization then took place from isopropanol. White crystals with a melting point of 148° to 151° C. were obtained.

(d) 2,4-diamino-5-(3-benzyloxy-4-methoxybenzyl)-pyrimidine:

92.6 g (0.25 mole) of anilinomethylidene-3-benzyloxy-4methoxydihydrocinnamicnitrile were heated to boiling for 22 hours with 38.2 g (0.4 mole) of guanidine hydrochloride and 30.25 g (0.56 mole) of sodiummethoxide in 600 ml ethanol. The mixture was allowed to cool to ambient temperature, was mixed with 20 ml of concentrated ammonia, the precipitated substance was filtered off and washed with water. White crystals with a melting point of 210° to 213° C. were obtained.

(e) 2,4-diamino-5-(3-hydroxy-4-methoxybenzyl)-pyrimidine:

20.2 g (0.06 mole) of 2,4-diamino-5-(3-benzyloxy-4-methoxybenzyl)-pyrimidine were hydrogenated with 4 g of palladium/5% charcoal in 250 ml of ethyleneglycol monomethylether for 45 minutes at 3 bar and 45° C. The solution was filtered, poured on to 600 ml of water, mixed with 10 ml of concentrated ammonia and the precipitated substance was filtered off. For recrystallization purposes, the substance was dissolved in boiling water accompanied by the addition of dilute hydrochloric acid. This was followed by filtration, adjusting to pH 8 with concentrated ammonia and slow cooling to ambient temperature. White crystals with a melting point of 208° to 210° C. were obtained.

(f) 2,4-diamino-5-[4-methoxy-3-(4'-nitrophenyl-4-sulphonylphenyl)-methoxybenzyl]-pyrimidine:

6.65 g (0.027 mole) of 2,4-diamino-5-(3-hydroxy-4-methoxybenzyl)-pyrimidine were dissolved in 30 ml of ethyleneglycol monomethylether, accompanied by the addition of 1.46 g (0.027 mole) of sodiummethoxide. The solution was added dropwise in 5 hours to a suspension of 9.64 g (0.027 mole) of 4-bromomethyl-4'-nitrodiphenylsulphone (J. Chem. Soc., 22, 1508, 1957) accompanied by stirring and at ambient temperature. The mixture was allowed to stand overnight, the precipitated substance was filtered off and washed with a little ethanol. It was then recrystallized from ethyleneglycol monomethylether. Yellowish crystals with melting point of 234° to 238° C. were obtained.

EXAMPLE 6

Preparation of 2,4-diamino-5-(4-methoxy-3-[2-(4'-nitrophenyl-4-sulphonylphenylamino)-ethoxy]-benzyl)-pyrimidine (K 132)

3 g (0.0122 mole) 2,4-diamino-5-(3-hydroxy-4-methoxybenzyl)pyrimidine (cf. example 5) were dissolved in 15 ml of ethyleneglycol monomethylether, accompanied by the addition of 0.66 g (0.0122 mole) of sodium methoxide and were added dropwise within 8 hours to a suspension of 4.7 g (0.0122 mole) of 4-N-(2-bromomethyl)-amino-4'-nitrodiphenylsulphone (cf. example 3c) in 20 ml of ethyleneglycol monomethylether, followed by stirring for a further 3 days at ambient temperature. The further preparation was as in example 5 (f). Recrystallization took place from ethyleneglycol monomethylether and yellow crystals with a melting point of 178° to 182° C. were obtained. According to the elementary analysis, the substance crystallizes with 0.5 mole of $H_2O$.

EXAMPLE 7

2,4-diamino-5-(4-methoxy-3-[3-(4'-nitrophenyl-4-sulphonylphenylamino)-propoxy]-benzyl)-pyrimidine (K 135) 3 g (0.0122 mole) of 2,4-diamino-5-(3-hydroxy-4-methoxybenzyl)pyrimidine (cf. example 5) were dissolved in 15 ml of ethyleneglycol monomethylether, accompanied by the addition of 0.66 g (0.0122 mole) of sodiummethoxide and in accordance with example 5 added dropwise to a suspension of 4.9 g of 4-[N-(3-bromopropyl)-amino] -4'-nitrodiphenylsulphone in 20 ml of ethyleneglycol monomethylether and stirred for 3 days at ambient temperature. The precipitated substance was filtered off and washed with ethanol and a little acetone. Subsequently recrystallization took place from acetone and ethyleneglycol monomethylether. Yellow crystals with a melting point of 131° to 134° C. were obtained.

EXAMPLE 8

Preparation of 2,4-diamino-5-[3-methoxy-4-(4'-nitrophenyl-4-sulphonylphenyl)-methoxybenzyl]-pyrimidine (K 116)

(a) 4-benzyloxy-3-methoxybenzaldehyde:

Starting with 4-hydroxy-3-methoxybenzaldehyde the procedure of example 5 (a) was used and white crystals with a melting point of 63° to 64° C. were obtained.

(b) 4-benzyloxy-3-methoxy-morpholinomethylidene dihydrocinnamic nitrile:

The procedure of example 5 (b) was adopted and the viscous crude product further processed.

(c) Anilinomethylidene-4-benzyloxy-3-methoxydihydrocinnamicnitrile:

Reaction took place as in example 5 c) and white crystals with a melting point of 119° to 121° C. were obtained.

(d) 2,4-diamino-5-(4-benzyloxy-3-methoxybenzyl)-pyrimidine:

The procedure of example 5 d) was adopted and white crystals with a melting point of 161° to 163° C. were obtained.

(e) 2,4-diamino-5-(4-hydroxy-3-methoxybenzyl)-pyrimidine:

The reaction took place as in example 5 e) and white crystals with a melting point of 266° to 267° C. were obtained.

(f) 2,4-diamino-5-[3-methoxy-4-(4'-nitrophenyl-4-sulphonylphenyl)-methoxybenzyl]-pyrimidine:

The reaction took place as in example 5 f) and yellow crystals with a melting point of 210° to 213° C. were obtained.

EXAMPLE 9

Preparation of
2,4-diamino-5-(4-[3-(4'-aminophenyl-4-sulphonyl-phenylamino)-propoxy]-3,5-dimethoxybenzyl)-pyrimidine (K 130)

(a) 4-amino-4'-[N-(3-bromopropyl)-amino]-diphenylsulphone 6 g (0.015 mole) of 4-[N-(3-bromopropyl)-amino]-4' nitrodiphenylsulphone were hydrogenated in 200 ml of methanol with Raney nickel (W2) for 60 minutes, at 40° C. and 4 bar. The solution was filtered, rotated in vacuo to 80 ml and placed cool. The precipitated substance was filtered off and recrystallized from methanol or methanol/water. A white substance was obtained, which discoloured in air and had a melting point of 115° to 119° C.

(b) 2,4-diamino-5-(4-[3-(4' aminophenyl-4-sulphonyl-phenylamino)propoxy]-3,5-dimethoxybenzyl)-pyrimidine:

A phenolate solution was prepared from 2.5 g of 2,4-diamino-5-(4-hydroxy-3,5-dimethoxybenzyl)-pyrimidine (cf. example 1) and 0.21 g of sodium in 60 ml of ethyleneglycol monomethylether, 3.4 g (0.092 mole) of 4-amino-4' -N-(3-bromopropyl)-aminodiphenylsulphone and 50 mg of sodiumiodide were added and this solution was stirred for 3 days at ambient temperature. The solution was poured on to 400 ml of ice, the precipitated substance was filtered off dissolved in 200 ml of dilute sulphuric acid, accompanied by heating to 45° C., filtered and adjusted to pH 8 with 3N sodium hydroxide solution, accompanied by cooling. The precipitated substance was filtered off and recrystalized from ethyleneglycol monomethylether or reprecipitated from dilute sulphuric or hydrochloric acid. A white substance with a melting point of 203 ° to 205° C. was obtained.

EXAMPLE 10

2,4-diamino-5-[4-(4' -aminophenyl-4-sulphonyl-phenylmethoxy)-3,5-dimethoxybenzyl]-pyrimidine (K 96) 1.8 g (0.0033 mols) of 2,4-diamino-5-[3,5-dimethoxy-4-(4'-nitrophenyl-4-sulphonylphenyl)-methoxybenzyl]-pyrimidine were hydrogenated in 40 ml of methanol at 50° C. and normal pressure for hours with Raney nickel W2 (Org. Synth. Coll. vol. 3).

The solution was filtered, heated to boiling, mixed with water in the boiling heat until the first permanent turbidity occurred, placed cool and the precipitated substance was filtered off. Recrystallization took place from ethyleneglycol monomethylether/water (see above) and a white substance with a melting point of 243° -246° C. was obtained.

EXAMPLE 11

2,4-diamino-5-(4-[2-(4' -aminophenyl-4-sulphonyl-phenylamino)-ethoxy]-3,5-dimethoxybenzyl)-pyrimidine (K 107) 1.2 g (0.002 mole) of 2,4-diamino-5-(3,5-dimethoxy-4-[2-(4'-nitrophenyl-4-sulphonyl-phenylamino)-ethoxy]-benzyl)-pyrimidine of Example 3 were hydrogenated in 50 ml of ethyleneglycol monomethylether at 50° C., a pressure of 3 bar and with Raney nickel W2 (cf. example 10) for 4 hours. The solution was filtered, mixed with 500 ml of water and cooled in the icebath. The precipitated substance was filtered off and recrystallized from ethyleneglycol monomethylether/water or reprecipitated from 3N sulphuric acid (cf. example 9 b)). A white substance with a melting point of 127° to 130° C. was obtained. According to elementary analysis, the substance crystallized with 1 mole of $H_2O$.

2,4-diamino-5-(4-[2-2' -methyl-4' -aminophenyl-4-sulphonyl-phenylamino)-ethoxy]-3,5-dimethoxybenzyl)-pyrimidine (K-151) was prepared according to the same process.

EXAMPLE 12

2,4-diamino-5-(4-[3-(4' -aminophenyl-4-sulphonylphenylamino)-propoxy]-3,5-dimethoxybenzyl)-pyrimidine (K 130)

3.6 g (0.006 mole) of 2,4-diamino-5-(3,5-dimethoxy-4-[3-(4'-nitrophenyl-4-sulphonylphenyl)-propoxy]-benzyl)-pyrimidine were hydrogenated in a mixture of 40 ml of ethyleneglycol monomethylether and 160 ml of methanol for 80 minutes, at 50° C. and 5 bar with Raney nickel.

The solution was filtered, mixed with 1000 ml of water, acidified with dilute hydrochloric acid, filtered again and adjusted to pH 8, accompanied by ice cooling with dilute ammonia. The precipitated substance was filtered off and well dried. It was recrystallized or reprecipitated from ethyleneglycol monomethylether/water (cf. example 9 b) and a white substance with a melting point of 203° to2205° C. was obtained.

EXAMPLE 13

2,4-diamino-5-[3-(4' -aminophenyl-4-sulphonylphenylmethoxy)-4-methoxybenzyl]-pyrimidine (K 128)

The compound of Example 5 was used as a starting compound. The reaction took place as in example 10. Recrystallization took place from methanol or ethyleneglycol monomethylether/water and a white substance with a melting point of 215° to 218° C. was obtained.

EXAMPLE 14

2,4-diamino-5-(3-[2-(4' -aminophenyl-4-sulphonylphenylamino)-ethoxy]-4-methoxybenzyl)-pyrimidine (K 138)

The reaction took place as in example 11. Recrystallization or reprecipitation took place from ethyleneglycol monomethylether/water or methanol (cf. example 9 b)) and a white substance with a melting point of 148° to 151° C. was obtained.

EXAMPLE 15

2,4-diamino-5-(3-[3-(4' -aminophenyl-4-sulphonylphenylamino)-propoxy]-4-methoxybenzyl)-pyrimidine (K 137)

The reaction took place as in example 14 and a white substance with a melting point of 207° to 210° C. was obtained.

EXAMPLE 16

2,4-diamino-5-[4-(4'-aminophenyl-4-sulphonylphenylmethoxy)-3-methoxybenzyl]-pyrimidine (K 120)

The compound of Example 8 was used as a starting compound. The reaction took place as in example 11 and a beige substance with a melting point of 220° to 222° C. was obtained.

EXAMPLE 17

2,4-diamino-5(4-[3-(4'-methylphenyl-4-sulphonyl-phenylamino)-propoxy]-3,5-dimethoxybenzyl)-pyrimidine (K 150)

(a) 4-amino-4'-methyldiphenylsulphide:

19.6 g (0.08 mole) of -nitro-4'-methyldiphenylsulphide (J. Chem. Soc., 22, 1508, 1957) were hydrogenated with Raney nickel W2 for 6 hours, at 45° C. and 4 bar in 275 ml of methanol.

The solution was then filtered from the Raney nickel, mixed with 600 ml of water, adjusted to pH 8 with concentrated ammonia and filtered. Recrystallization then took place from methanol or reprecipitation from 3N hydrochloric acid. White crystals of melting point 182° C were obtained.

(b) 4-tosylamino-4'-methyldiphenylsulphide:

15 g (0.07 mole) of 4-amino-4'-methyldiphenylsulphide were mixed in 75 ml of pyridine with 14.7 g (0.077 mole) of toluene sulphochloride and stirred for 2 hours at room temperature.

The solution was then mixed with a mixture of 100 ml of ethanol and 80 ml of water, cooled in the icebath, the precipitated substance was filtered off and washed with a great amount of water. Recrystallization took place from ethanol and white crystals with a melting point of 147° to 149° C. were obtained.

(c) 4-N-(3-bromopropyl)-N-tosylamino-4'-methyldiphenylsulphide:

Reaction took place as in example 4 a). Recrystallization took place in methanol and white crystals with a melting point of 113° to 115° C. were obtained.

(d) 4-[N-(3-bromopropyl)-N-tosylamino]-4'-methyldiphenylsulphone:

Reaction took place as in example 4 b). Recrystallization took place in methanol and white crystals with a melting point of 137° to 138° C. were obtained.

(e) 4-[N-(3-bromopropyl)-amino]-4'-methyldiphenylsulphone:

Reaction took place as in example 4 c). Recrystallization took place in methanol and white crystals with a melting point of 125° to 127° C. were obtained.

(f) 2,4-diamino-5-(4-[3-(4'-methylphenyl-4-sulphonyl-phenylamino)propoxy]-3,5-dimethoxybenzyl)-pyrimidine:

Reaction took place as in example 3 d). 90 parts of methylene chloride, 10 parts of methanol and 1 part of concentrated ammonia served as the mobile phase mixture. The fraction was rotated dryness and the white substance left behind was recrystallized from methanol. White crystals with a melting point of 157° to 158° C. were obtained.

EXAMPLE 18

Demonstration of the inhibiting activity of the substances of the invention against mycobacteria The minimum inhibiting concentration of the commercially available substances and the substances of the invention given in table 1 were determined by standard methods ("Methoden zur Empfindlichkeitsprufung von bakteriellen Krankheitserregern", DIN 58940, TEIL 5).

The determination took place on the following bacterial cultures:

1. Mycobacterium lufu (F. Portaels, Amls. Soc. belg. Meol. trop. 60, 381 (1980)) FIB 1-85 JS
2. Mycobacterium tuberculosis H 37 RV, FIB 2-85 JS
3. Mycobacterium marinum SN 1254, FIB 3-85 JS
4. Escherichia coli, FIB 4 4-85 JS The above strains have been deposited with the indicated numbers in the Culture Collection of the Forschungsinstitut Borstel, Parkallee 1-42, 2061 Borstel, Federal Republic Germany.

For culturing the bacterial cultures use was made of nutrient substrates according to Gottsacker and Lowenstein Jensen, as well as culture media according to Lockemann or Dubos-Davis (cf. "Nachweisverfahren furMMycobakterien aus Untersuchungsmaterial,, III, Nahrbodenrezepte zur Kultur von Tuberkulosebakterien" 1978, publisher: Deutsches Zentralkomitee zur Bekampfun9 der Tuberculose, Poppenhusenstrasse 14c, 2000 Hamburg 60).

In each case $5 \times 10^{-3}$ to $5 \times 10^{-5}$ mg, based on the wet weight, of the mycobacteria strains were incubated in 2 ml of culture fluid (Lockemann+0.5 wt./vol.% of bovine serum albuminfraction 5, see above) at 31° C. with graded concentrations of the particular inhibitor (dilution series). Depending on the bacteria strain, the culture tubes were read after 8 to 15 days.

The minimum inhibiting concentration (MIC) is the inhibitor concentration in $\mu$mole/$\upsilon$, at which no multiplication of the inoculated cell is detected.

The results are given in table 1 and show that the compounds of the invention have a 300 times higher antimycobacterial activity than the comparison products (cf. minimum inhibiting concentration of pyrimethamine and the inventive compound K 130 for Mycobacterium lufu).

TABLE 1

| Substance | Bacterial-kinetics $I_{50}$ [$\mu$Mmol/l] M. lufu | Minimal inhibition concentration ($\mu$Mmol/l) | | | |
|---|---|---|---|---|---|
| | | M. lufu H37Rv | M. tub. SN1254 | M. marin. | E. coli |
| Trimethoprim | 95 | >110 | >110 | 28 | 1,4 |
| Brodimoprim | 45 | 80 | 94 | 18 | 1,4 |
| Tetroxoprim | 213 | — | 71 | — | 11,25 |
| Diaveridin | — | >123 | >123 | 46 | 8 |
| Pyrimethamin | — | 210 | 129 | — | — |
| GH 003 | — | 24 | 12 | 6 | 32 |
| GH 103 | — | 44 | 22 | 22 | 16 |
| GH 305 | — | 25,3 | 51 | 51 | 22,5 |
| GH 306 | — | 56,5 | 56 | 28 | — |
| GH 307 | — | 23 | 46 | 35 | >45 |
| GH 308 | — | 22,3 | 33 | 5,6 | 22,5 |
| GH 309 | — | 21,5 | 11 | 5,4 | 8,0 |
| GH 310 | — | 20,7 | 15 | 2,4 | 4,0 |
| K 95 | — | 58 | 29 | 29 | — |
| K 96 | — | 31 | >62 | >62 | >90 |
| K 107 | 1,37 | 1,8 | 33 | 3,6 | >45 |
| K 120 | — | 32,0 | 65 | 33 | >90 |
| K 122 | — | >58 | 3,4 | 13 | 11,25 |
| K 128 | 8,31 | 12,2 | 65 | 6,1 | >45 |
| K 130 | 1,66 | 0,7 | 4,0 | 6,2 | 32 |
| K 132 | — | 11,0 | 7,3 | 15 | 11 |
| K 135 | — | 10,6 | 7,1 | 14 | 11 |
| K 137 | — | 2,3 | 2,1 | 26 | >90 |
| K 138 | — | 3,8 | 11,5 | 7,7 | — |
| K 150 | — | 28 | 28 | — | — |

Determination also took place of the minimum inhibiting concentration of compound GH 310, as given above, relative to a number of intracellular mycobacteria isolated from patients in accordance with known processes ("Isolierung von Mycobakteriun", DIN 58943, Part 3, 1980). The results are given in table 2.

TABLE 2

| Mycobacterium | | Minimum Inhibiting Concentration GH 310 μmole/t |
|---|---|---|
| M. smegmatis | FIB 5-85 JS | 20 |
| M. avium | FIB 6-85 JS | 5.2 |
| M. kansasii | FIB 7-85 JS | 5.2 |
| M. simiae | FIB 8-85 JS | 2.6 |

EXAMPLE 19

The half maximum inhibiting concentration ($I_{50}$) of the commercially available and inventive substances given in table 1 was determined for Mycobacterium lufu (F. Portaels, see above) according to the bacteria multiplication kinetics method (J. K. Seydel et al, Chemotherapie 29, 249, 1983).

For this purpose a fresh 4 to 6 week old Mycobacterium lufu culture from a Gottsacker nutrient substrate was inoculated into fresh modified Dubos-Davis medium +Q-2.wt/vol% bovine serum albumin-fraction 5 ("Nahrbodenrezepte zur Kulurvon Tuberculosebakterien"—see above). In order to obtain a uniform suspension, the bacterial cells were homogenized in a homogenizer in 5 ml of medium (Potter S). The suspension was diluted with 15 ml of medium and centrifuged at 150 g for 4 minutes. Part of the supernatant was immediately used for determining the number of cells and the remaining part was used for mixing the culture. For this purpose, the suspension was subsequently diluted with the medium in such a manner that it contained approximately $10^5$ bacteria cells/ml. 50 ml portions of the culture were then transferred into 300 ml Erlenmeyer flasks, which were equipped with a 2 cm magnetic stirrer and the inhibitor was added. The inhibitor concentrations were graded in such a manner that a perfect calculation of the $I_{50}$ values was possible (cf. FIGS. 1 and 2). The cultures were kept at 31° C. and samples were taken at 20 to 30 hour intervals over a total period of 330 hours and the total number of cells was determined.

The cell number determination was carried out by taking 1 ml samples from the cultures and diluting the same with a particle-free aqueous solution containing 5% common salt and 0.5% formaldehyde so that bacteria numbers between 500 and 90,000 were obtained. The dilute solutions were measured with a Coulter counter model ZM, equipped with a 30 μm capillary.

The number of bacteria in 50 μl was determined with the following instrument setting:

| | |
|---|---|
| Magnification | 2 |
| Current | 999 μA |
| Matching | 5 kOhm |
| Lower threshold | 7 |
| Upper threshold | Open (J. K. Seydel, E. Wempe and M. Rosenfeld, Chemotherapie, 29, 249, 1983). |

The results of the multiplication kinetics to M. lufu in the presence of compounds K 107 or K 130 are given in FIGS. 1 and 2 and the $I_{50}$ values in table 1.

EXAMPLE 20

Determination of the minimum inhibiting concentration of combinations of inventive compounds with diaminodiphenylsulphone (DDS)

The minimum inhibiting concentration of combinations of inventive compounds K 107 and K 130 with DDS for mycobacterium lufu was determined by Chessboard-titrations (see above) (cf. Berenbaum, M.C., J. Infect. Dis., 137; pp122-130, 1978 and J. K. Seydel et al, see above). The bacteria were incubated under the conditions of example 18.

A bidimensional dilution series was prepared, the components being present in the quantities according to tables 3 and 4.

The sum of the fractional inhibiting concentrations (FII) was calculated according to the equation of C. W. Norden et al, J. Infect. Dis., 140, 290, 1978:

$$FII = \frac{\text{Minimum inhibiting concentration of compound A in combination}}{\text{Minimum inhibiting concentration of compound A alone}} + \frac{\text{Minimum inhibiting concentration of compound B in combination}}{\text{Minimum inhibiting concentration of compound B alone}}$$

With FII <1 synergism exists, whereas FII >>1 means antagonism. The results are given in tables 3 and 4; they show that nearly each of the chosen mixing ratios led to a synergistic effect.

The FII for some of the mixing ratios are given in tables 3 and 4.

TABLE 3

| | ← K 130 [μm/ml] — Microorganism: *M. lufu* | | | | | | | | | | | |
|---|---|---|---|---|---|---|---|---|---|---|---|---|
| | | 0,4 | 0,36 | 0,32 | 0,28 | 0,24 | 0,20 | 0,16 | 0,12 | 0,08 | 0,04 | 0 |
| ↑ | 0,2 | | | | | | | | | | | – |
| | 0,018 | | | | | | | | | | | – |
| | 0,016 | | | | | | | | | | | (+) |
| | 0,014 | | | | | | | | | | | (+) |
| DDS | 0,012 | | | | | | | | | | | + |

TABLE 3-continued

| | | | | | K 130 [μm/ml] | | | | | | | Microorganism: M. lufu |
|---|---|---|---|---|---|---|---|---|---|---|---|---|
| | | 0,4 | 0,36 | 0,32 | 0,28 | 0,24 | 0,20 | 0,16 | 0,12 | 0,08 | 0,04 | 0 |
| [μg/ml] | 0,01 | | | | | | | | | 1* | + | ++ |
| | 0,008 | | | | | | | | | (+) | + | ++ |
| | 0,006 | | | | | | | 2* | + | + | ++ | +++ |
| | 0,004 | | | | 3* | | + | ++ | ++ | +++ | +++ | +++ |
| | 0,002 | | | | (+) | ++ | +++ | +++ | +++ | +++ | +++ | +++ |
| | 0 | | (+) | ++ | ++ | +++ | +++ | +++ | +++ | +++ | +++ | |

1* FII = 0.75
2* FII = 0.73
3* FII = 0.92
Dubos + 0,5% Albumin
+++ = growth as control
++ = slight growth inhibition
+ = strong growth inhibition
− = complete growth inhibition

TABLE 4

| | | | | | DDS [μg/ml] | | | | | | Microorganism: M. lufu |
|---|---|---|---|---|---|---|---|---|---|---|---|
| | | 0,027 | 0,024 | 0,021 | 0,018 | 0,015 | 0,012 | 0,009 | 0,006 | 0,003 | 0,0 |
| | 2,40 | | | | | | | | | | − |
| | 2,16 | | | | | | | | | | − |
| | 1,92 | | | | | | | | | | (+) |
| | 1,68 | | | | | | | | | | (+) |
| K 107 | 1,44 | | | | | | | | | | (+) |
| [μg/ml] | 1,20 | | | | | | | | | 1* | (+) |
| | 0,96 | | | | | | | | | (+) | + |
| | 0,72 | | | | | | | 2* | (+) | + | ++ |
| | 0,48 | | | | | | (+) | + | + | ++ | +++ |
| | 0,24 | | | 3* | (+) | + | + | ++ | ++ | +++ | +++ |
| | 0,00 | − | (+) | (+) | + | + | ++ | +++ | +++ | +++ | |

1* FII = 0.68
2* FII = 0.45
3* FII = 0.98
Dubos + 0.5% Albumin
+++ = growth as control
++ = slight growth inhibition
+ = strong growth inhibition
− = complete growth inhibition

EXAMPLE 21

The synergistic activity of a combination of DDS and the inventive compound GH 306 was also demonstrated by determining the multiplication kinetics of M. lufu (see above) according to example 19.

Growth kinetics in the presence of inhibitors alone, as well as the combination were recorded. The results are given in FIG. 3 and reveal a drastic increase in activity through combining DDS and GH 306 for a constant overall concentration.

EXAMPLE 22

Combination product in tablet form

Tablets with the following composition were prepared by conventional processes:

| | |
|---|---|
| DDS | 100 mg |
| 2,4-diamino-5-(4-decyloxy-3-methoxybenzyl)-pyrimidine | 100 mg |
| Lactose | 150 mg |
| Primojel (starch derivative) | 3 mg |
| Povidone K 30 (polyvinylpyrrolidone) | 4 mg |
| Magnesium stearate | 3 mg |
| Total Weight | 360 mg |

We claim:

1. A compound selected from 2, 4-Diamino-5-benzyl-pyrimidines according to formula I

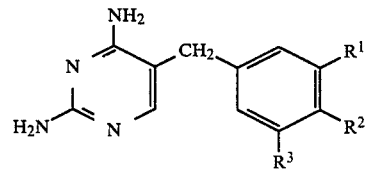

wherein one of the substituents $R^1$ to $R^3$ is a $2^1$ to $R^3$ is a 2′, 2′-substituted phenyl-4-sulphonylphenyl aminoalkoxy, phenyl-4 -sulphonylphenylaminoalkylthio, phenyl-4-sulphonylphenylalkoxy or phenyl-4-sulphonylphenylalkylthio group, in which the substituents in the 2′, 4′-position are the same or different and are hydrogen, amino, alkylamino, dialkylamino, alkoxy, alkyl, nitro, alkylthio and/or acetamino groups wherein the alkyl radical has 1 to 6 carbon atoms in the chain and the two other substituents $R^1$ to $R^3$ are the same or different and are hydrogen, alkoxy, alklythio and/or alkylamino groups, the alkyl radical of the two other substituents having 1 to 3 carbon atoms.

2. 2,4diamino-5-[3,5-dimethoxy-4(4″-nitrophenyl-4-sulphonylphenyl)-methoxybenzyl]-pyrimidine.

3. 2,4-diamino-5-(3,5-dimethoxy-4-[3-(4′-nitrophenyl-4-sulphonylphenylamino)propoxy]benzyl)-pyrimidine.

4. 2,4-diamino-5-(4-methoxy-3-[2-(4'-nitrophenyl-4-sulphonylphenylamino)ethoxy]benzyl)-pyrimidine.

5. 2,4-diamino-5-(4-methoxy-3-[3-(4'-nitrophenyl-4sulphonylphenylamino)propoxy]benzyl)-pyrimidine.

6. 2,4-diamino-5-[4-(4'-aminophenyl-4-sulphonylphenylmethoxy)-3,5-dimethoxybenzyl]-pyrimidine.

7. 2,4-diamino-5-(4-[3-(4'-aminophenyl-4-sulphonylphenylamino)-propoxy]-3,5-dimethoxybenzyl)-pyrimidine.

8. 2,4-diamino-5-[3-(4'-aminophenyl-4-sulphonylphenylmethoxy)-4-methoxybenzyl]-pyrimidine.

9. 2,4-diamino-5-(3-[2-(4'-aminophenyl-4-sulphonylphenylamino)-ethoxy]-4-methoxybenzyl)-pyrimidine.

10. 2,4-diamino-5-(4-[3-(4'-aminophenyl-4sulphonylphenylamino)propoxy]-3,5-dimethoxybenzyl)-pyrimidine.

11. 2,4-diamino-5-[4-(4'-aminophenyl-4-sulphonylphenylmethoxy)-3-methoxybenzyl]-pyrimidine.

12. 2,4-diamino-5-(4-[3-(4'-methylphenyl-4-sulphonylphenylamino)-propoxy]-3,5-dimethoxybenzyl)-pyrimidine.

13. 2,4-diamino-5-(4-[2-(4'-aminophenyl-4-sulphonylphenylamino)-ethoxy]-3,5-dimethoxybenzyl)-pyrimidine.

14. 2,4-diamino-5-(4-[2-(2'-methyl-4'-aminophenyl-4sulphonylphenylamino)ethoxy]-3,5-dimethoxybenzyl)-pyrimidine.

15. Physiologically acceptable acid addition salts of the compounds according to claim 3 with inorganic or organic acids.

16. Process for the preparation of the 2,4-diamino-5-benzyl pyrimidines according to claim 1 characterized in that either.

(a) a compound according to formula II

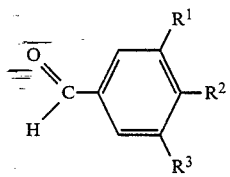

in which one of the substituents $R^1$ to $R^3$ is a hydroxyl or a mercapto group and the two other or the substituents $R^1$ to $R^3$ are the same or different and are hydrogen, alkoxy, alkylthio and/or alkyl-amino groups is etherified with a compound according to formula III

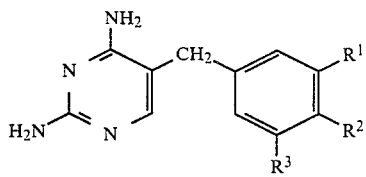

or formula IV

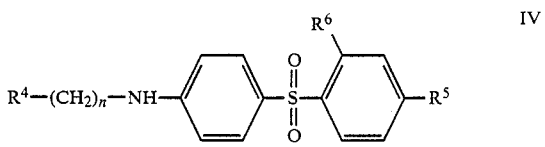

in which $R^4$ is a halogen and $R^5$ and $R^6$ are the same or different and are hydrogen, amino, alkylamino, dialkylamino, alkoxy, alkyl, nitro, alkylthio and/or acetamino groups.

17. A pharmaceutical composition characterized in that it contains a compound according to claim 1, as agent with antimicrobial activity together with a pharmaceutically acceptable carrier.

18. A pharmaceutical composition, according to claim 17, combined with inhibitors of the type of diaminodiphenylsulphones, ring-substituted 4-aminodiphenylsulphones or ring and/or nitrogen-substituted diaminodiphenylsulphones together with a pharmaceutically acceptable carrier.

19. A pharmaceutical composition, according to claim 18, characterized in that it is combined with sulphonamides exhibiting antibacterial activity together with a pharmaceutically acceptable carrier.

20. A method of inhibiting infectious growth which comprises treating microbial infections with a growth inhibiting amount of a compound according to claim 1.

21. A method according to claim 20 of wherein said compound is combined with an inhibitor selected from diaminodiphenylsulphones or ring and/or nitrogen-substituted diaminodiphenylsulphones and/or antibacterially active sulphonamides.

* * * * *